(12) United States Patent
Sawatari et al.

(10) Patent No.: US 7,476,131 B2
(45) Date of Patent: Jan. 13, 2009

(54) DEVICE FOR REDUCING CROSSTALK

(75) Inventors: Ken Sawatari, San Jose, CA (US); Paul D. Mannheimer, Danville, CA (US); Bradford B. Chew, San Ramon, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 0 days.

(21) Appl. No.: 11/540,376

(22) Filed: Sep. 29, 2006

(65) Prior Publication Data

US 2008/0081508 A1    Apr. 3, 2008

(51) Int. Cl.
 *H01R 24/00*    (2006.01)
(52) U.S. Cl. ..................................... 439/676
(58) Field of Classification Search ............... 439/676, 439/418, 76.1; 600/323, 325, 344
 See application file for complete search history.

(56) References Cited

U.S. PATENT DOCUMENTS

| | | | | |
|---|---|---|---|---|
| 5,109,849 A | * | 5/1992 | Goodman et al. ........... 600/483 |
| 5,237,994 A | * | 8/1993 | Goldberger ................. 600/323 |
| 5,246,003 A | * | 9/1993 | DeLonzor .................... 600/344 |
| 5,249,576 A | * | 10/1993 | Goldberger et al. ......... 600/323 |
| 5,411,024 A | * | 5/1995 | Thomas et al. .............. 600/325 |
| 5,599,209 A | | 2/1997 | Belopolsky |
| 6,007,368 A | | 12/1999 | Lorenz et al. |
| 6,095,974 A | * | 8/2000 | Shemwell et al. ........... 600/310 |
| 6,112,107 A | * | 8/2000 | Hannula ...................... 600/310 |
| 6,116,965 A | | 9/2000 | Arnett et al. |
| 6,186,836 B1 | | 2/2001 | Ezawa et al. |
| 6,280,256 B1 | | 8/2001 | Belopolsky et al. |
| 6,325,660 B1 | * | 12/2001 | Diaz et al. ................... 439/418 |
| 6,379,175 B1 | | 4/2002 | Reede |
| 6,520,807 B2 | * | 2/2003 | Winings ..................... 439/676 |
| 6,731,805 B2 | * | 5/2004 | Brodsky et al. ............. 382/199 |
| 6,745,061 B1 | * | 6/2004 | Hicks et al. ................. 600/344 |
| 7,046,020 B2 | * | 5/2006 | LaMeres et al. ............ 324/754 |
| 2005/0079772 A1 | * | 4/2005 | DeLessert ................... 439/700 |
| 2007/0141869 A1 | * | 6/2007 | McNeely .................... 439/76.1 |

* cited by examiner

*Primary Examiner*—Chandrika Prasad (57) ABSTRACT

A device and method for reducing crosstalk between wires is provided. The method includes spatially separating first and second sets of wires. A device is disposed relative to the first and second sets of wires to maintain the spatial separation. The method also comprises coupling pins to the first and second sets of wires. Additionally, the method includes covering the device with a connector housing.

10 Claims, 8 Drawing Sheets

DEVICE FOR REDUCING CROSSTALK

TECHNICAL FIELD

The present invention relates generally to electronic devices, such as medical devices, and more particularly to reducing crosstalk in such devices.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Medical devices such as those used for monitoring a patient's vital sign or other physiologic variable, are commonly comprised of a patient-contacting signal transducer and a monitor that connects to the transducer, processes the signals, and provides information to the caregiver. Typically, the transducer is connected to the monitor with and interface cable that includes wires for conducting electrical signals.

An ideal cable and connector assembly for use in such medical devices would be immune to noise interference from external sources as well as crosstalk between wires within the cable and connector assembly. In reality, however, the manufacturing process of a cable and connector assembly includes steps that make the wires within a cable and connector assembly vulnerable to noise, such as capacitive and inductive crosstalk, wherein electrical signals in one wire or pair of wires may interfere or create noise on a nearby wire. The crosstalk may be detrimental to the operation of a medical device. For example, in pulse oximetry, the crosstalk can result in inaccurate readings of $SpO_2$ values.

Cables are generally manufactured to limit the amount of external noise and inductive and capacitive crosstalk that can occur between wires. For example, the cables are bundled together with an electrically insulating protective coating and a conductive shield mesh to protect against environmental noise sources. Additionally, the cables may be made up of twisted wire pairs, commonly referred to as twisted pairs. As their name suggests, the twisted pairs are a pair of wires twisted together in a manner that results in each wire becoming exposed to the same or similar amounts noise elements such that the noise can be nearly or completely canceled out. A twisted pair may be surrounded by an electrically grounded conductive mesh shield to help eliminate noise interference from other wires within the cable bundle. Twisted pairs having the conductive mesh shield are referred to as shielded twisted pairs, while twisted pairs without the conductive mesh are referred to as unshielded twisted pairs. The cables used in medical devices such as pulse oximetry systems are commonly constructed with one or both types of twisted pairs, where multiple sets of wires are combined into a cable bundle. Electrical crosstalk can occur when signal wires electrically contact one another (a "short"), or come into close proximity to adjacent conductors.

In order to connect the wires to connector pins, the cable bundle must be stripped and the wires untwisted. Thus, in this section of the cables, the wires are unprotected and vulnerable to crosstalk interference. Furthermore, after the wires have been connected to connector pins and the pins are placed in a connector housing, even if the wires are initially pushed apart and spatially separated, additional handling and processing may push the wires together and increase the likelihood of crosstalk.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a medical device cable. In the examples used herein, the medical device is a pulse oximeter. The pulse oximeter cable comprises a first pair of wires, a second pair of wires and an insulative piece configured to maintain spatial separation between the first and second pairs of wires. Additionally, the cable comprises a connector housing formed over the insulative piece.

In accordance with another aspect of the present invention, there is provided a method of manufacturing an electrical cable comprising spatially separating a first set of wires from a second set of wires and disposing a device relative to the first and second sets of wires to maintain the spatial separation and coupling pins to the first and second sets of wires. Additionally, the method comprises covering the device with a connector housing.

BRIEF DESCRIPTION OF THE DRAWINGS

Certain exemplary embodiments are described in the following detailed description and in reference to the drawings in which.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
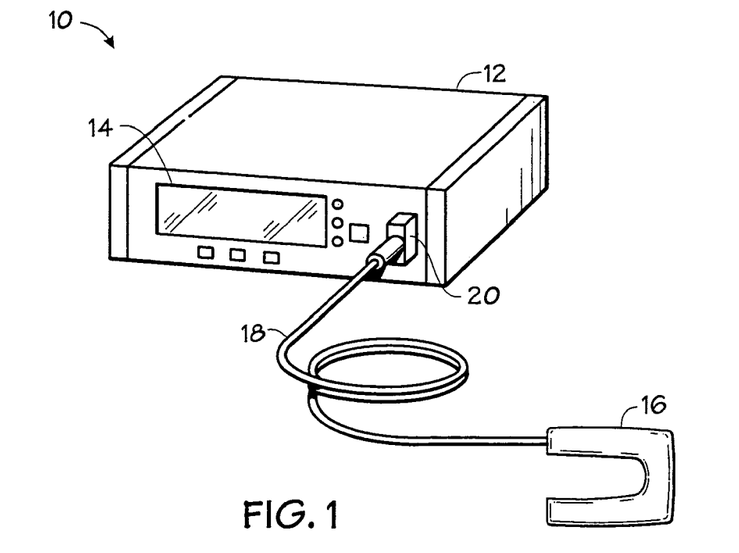
FIG. 1 illustrates an exemplary pulse oximetry system in accordance with an exemplary embodiment of the present invention.

Turning initially to FIG. 1, an exemplary medical device, such as a pulse oximetry system, is illustrated and generally designated by the reference numeral 10. Pulse oximetry systems, such as system 10, calculate various physiological parameters by detecting electromagnetic radiation (light) that is scattered and absorbed by blood perfused tissue. The pulse oximeter system 10 has a main unit 12 which houses hardware and software configured to calculate various physiological parameters. The main unit 12 has a display 14 for displaying the calculated physiological parameters, such as oxygen saturation or pulse rate, to a caregiver or patient. The pulse oximetry system 10 also has a sensor unit 16, which may take various forms. As shown in FIG. 1, the sensor unit 16 may be configured to fit over a digit of a patient or a user. The sensor unit 16 is connected to the main unit 12 via a cable 18. The cable 18 may be coupled to main unit 12 using a connector housing 20. It is at the interface between the cable 18 and the pins 34 (shown in FIG. 2) of the connector housing 20 where noise interference in the form of crosstalk is most likely to occur.

Figure 2:
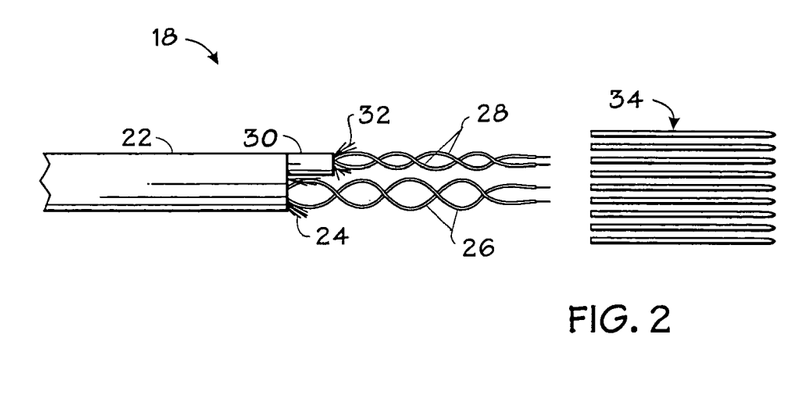
FIG. 2 illustrates a pulse oximetry cable in accordance with an embodiment of the present invention.

A more detailed illustration of the cable 18 is shown in FIG. 2. Specifically, the cable 18 is shown having an outer jacket 22. The outer jacket 22 is a polymeric material jacket to hold the cable bundle together and to protect the wires from environmental factors. Under the outer jacket 22, the cable 18 has an outer shield 24 which may be configured to prevent electromagnetic interference from external sources. The outer shield 24 may be made up any type of shielding material, such as a metallic mesh, for example.

The cable 18, as shown in FIG. 2, has both emitter wires 26 and detector wires 28. Both the emitter wires 26 and the detector wires 28 are twisted pair wires. The wire pairs are twisted so that each wire is similarly exposed to any potential electromagnetic interference that reaches the wires. Because each of the wires is exposed to similar levels of interference, the interference can be reduced through circuit designs that cancel such common-mode signals.

The emitter wires 26 may comprise an unshielded twisted pair and the detector wires 28 may comprise a shielded twisted pair. As can be seen in FIG. 2, the detector wires 28 have a jacket 30, such as a polymeric coating for example, and an inner shield 32 similar to the outer shield 24 of the cable 18. The detector wires 28 are shielded electrically to prevent potential crosstalk from the emitter wires 26, as well as interference from environmental factors. Both the emitter wires 26 and the detector wires 28 are individually connected to respective pins 34 of a connector housing, such as connector housing 20.

During the manufacturing process, the outer jacket 22 is stripped from the cable 18, and the coating 30 of the detector wires 28 is stripped from the detector wires 28. The emitter wires 26 and detector wires 28 are then untwisted to facilitate connection of the emitter wires 26 and detector wires 28 to their respective pins 34. The detector wires 28, however, become vulnerable to a variety of noise-inducing influences, including inductive and capacitive crosstalk from the emitter wires 26 when they are unshielded and untwisted.

Initially, during the manufacturing process, the emitter wires 26 and the detector wires 28 are separated. The wires may be pulled apart by a worker or a machine may push a tool in between the pairs of wires to separate them. Unfortunately, after this initial separation, little may be done to maintain the separation of the wires.

Although workers may understand their specific role in the manufacturing process, they may not fully appreciate the importance of maintaining the separation between the wires and may fail to take precautions to maintain the separation of the wires. As such, the cables may be tossed into bins for transportation to different workstations, and the cables may be handled and manipulated by multiple workers and machines before the cables are fully assembled and ready for operation In the bins, the cables may be compacted together or get tangled together. While being handled and manipulated by workers and machines, the wires may be pushed together. Therefore, at the end of the manufacturing process, there is a risk that the wires will no longer be separated, resulting in an increased susceptibility to crosstalk in the fully assembled cables.

Figure 3:
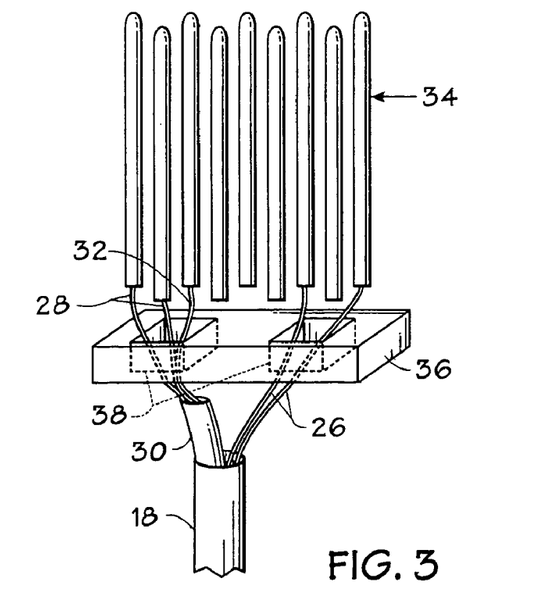
FIG. 3 illustrates an insulative material with slots through which wires pass in accordance with an exemplary embodiment of the present invention.

To address this concern, an insulative material 36, as illustrated in FIG. 3, may be used to maintain spatial separation between the emitter wires 26 and detector wires 28 in order to prevent crosstalk. The insulative material 36 may be a silicon rubber, polymer, or other electrically non-conductive material. The insulative material 36 may have apertures 38, such as slots, through which the emitter wires 26 and detector wires 28 are passed during the manufacturing process. The wires may be coupled to the pins before or after being passed through the apertures 38. The apertures 38 of the insulative material 36 help ensure that the emitter wires 26 and detector wires 28 remain separated throughout the manufacturing process to prevent crosstalk.

After the emitter wires 26 and detector wires 28 have been positioned in the apertures 38, the insulative material 36 and a portion of the pins 34 and the wires 26 and 28 are encapsulated by the connector housing 20. An over-molding process (such as insert, injection, or transfer molding), or other means, may be implemented to form the connector housing 20. The connector housing 20 is formed over the insulative piece 36 so that the insulative piece 36 can continue to prevent the emitter and detector wires from moving closer to each other during the encapsulation process. By preserving the spatial separation, the insulative piece 36 helps the detector wires 28 to be less susceptible to crosstalk interference from the emitter wires 26.

Figure 4:
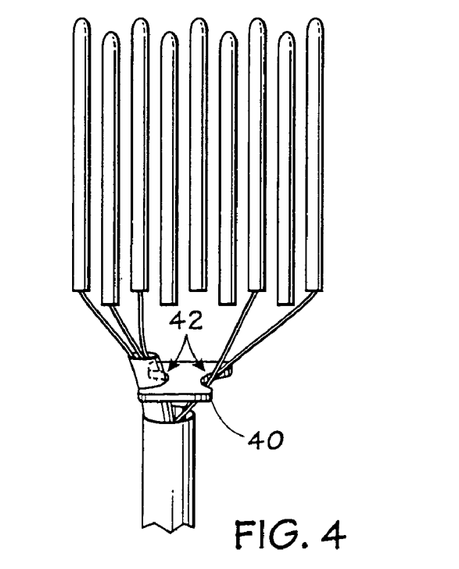
FIG. 4 illustrates an insulative piece between wires in accordance with an alternative exemplary embodiment of the present invention.

In another embodiment, as illustrated in FIG. 4, an insulative piece 40, such as a piece of silicon rubber, polymer or other electrically non-conductive material, may be wedged or coupled between the emitter wires 26 and detector wires 28 to prevent electrical crosstalk. The insulative piece 40 is wedged or coupled between the emitter wires 26 and detector wires 28 by directing the wires into open ended apertures 42 located on opposite sides of the insulative piece 40. The insulative piece 40 is installed prior to the encapsulation process and prevents the emitter wires 26 and the detector wires 28 from moving into closer proximity of each other during the encapsulation process or handling prior during the manufacturing process. The encapsulation process forms the connector housing 20 over the insulative piece 40, as described above.

Figure 5:
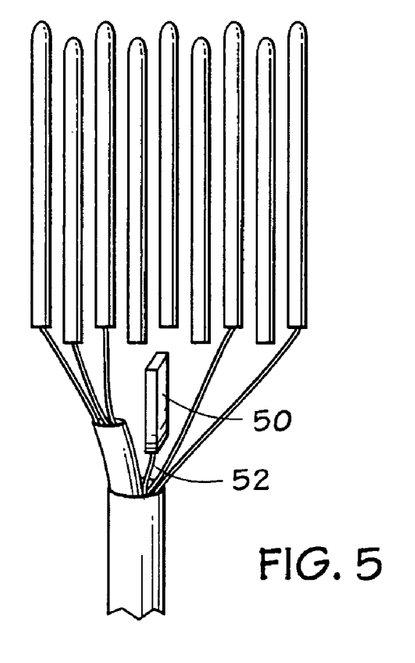
FIG. 5 illustrates an electrically grounded conductive object between wires in accordance with an alternative exemplary embodiment of the present invention.

Alternatively, as illustrated in FIG. 5, a conductive object 50, such as a piece of copper, positioned between the emitter wires 26 and detector wires 28 can help reduce or eliminate crosstalk. The conductive object 50 is electrically grounded via the wire 52. The wire 52 may be formed by aggregating the wire mesh of the outer shield 24 to form a single wire, or comprise a separate drain or ground wire. The conductive object 50 is positioned between the emitter wires 26 and detector wires 28. It should be understood that the conductive object 50 may be implemented alone or in conjunction with insulative embodiments described herein. Specifically, for example, the conductive object 50 may be supported by the insulative material 36 of FIG. 3. The connector housing 20 would then be formed over the both conductive object 50 and the insulative material 36.

Figure 6:
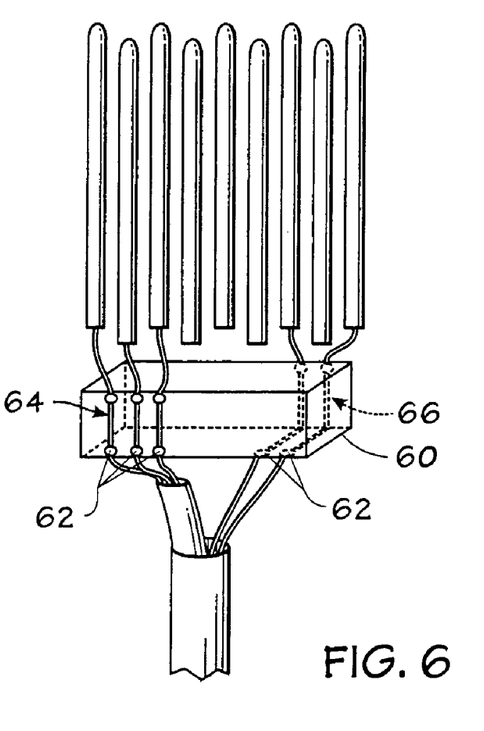
FIG. 6 illustrates an insulative block with pads and traces configured to spatially separate wires in accordance with an alternative exemplary embodiment of the present invention.

Turning to FIG. 6, yet another embodiment includes an insulative piece 60 with solder pads 62 and traces 64 and 66. The insulative piece 60 may be a resin glass composition, a polymer capable of withstanding the temperatures used in soldering, or other suitable material. As illustrated, the insulative piece 60 has solder pads 62 on one side to connect the emitter wires 26 and detector wires 28 to the insulative piece 60. The solder pads 62 are connected to electrically conductive traces 64 and 66 that run on the front side and backside of the insulative piece 60, respectively. Specifically, the traces 64, which are coupled to the detector wires 28, run on a front side of the insulative piece 60, while the traces 66, which are coupled to the emitter wires 26, run on a backside of the piece 60. Thus, the insulative piece 60 spatially separates the emitter traces 26 from the detector traces 28 to prevent crosstalk from occurring. Once the wires and pins are coupled to the insulative piece, the connector housing 20 may be formed over the insulative piece 60 through the encapsulation process.

Figure 7:
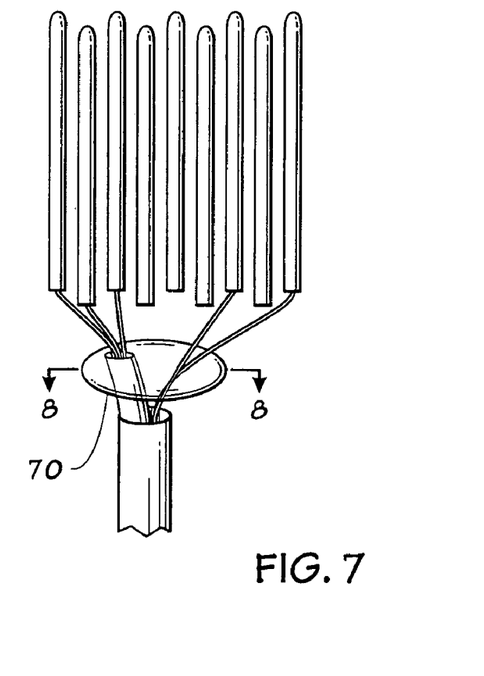
FIG. 7 illustrates placing an epoxy material on and in between wires in accordance with an alternative exemplary embodiment of the present invention.

Alternatively, an insulative material 70, such as epoxy resin or silicone, for example, may be used to maintain spatial separation of the detector wires 28 and the emitter wires 26, as illustrated in FIG. 7. The material 70 may be placed on and in between the wires 26 and 28 after the external coating has been removed and the wires 26 and 28 have been separated from each other. The material 70 may initially be a two-part gel that cures and hardens as the two parts interact. Once cured, the material 70 holds the wires in place to prevent the wires from coming into proximity of each other during the manufacturing process.

Figure 8:
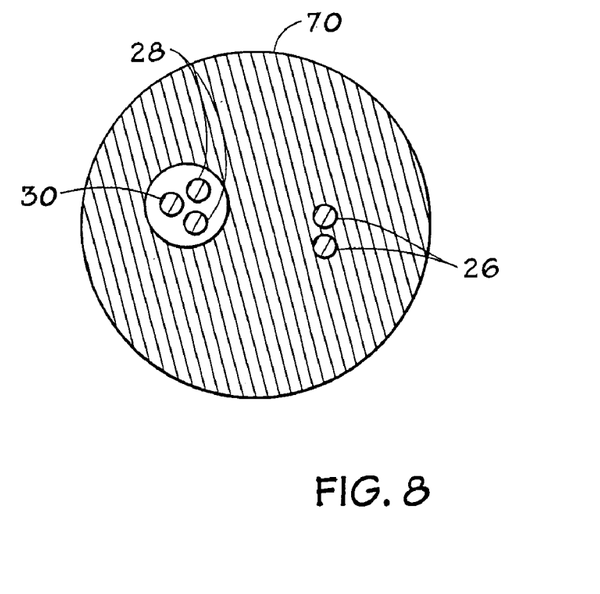
FIG. 8 illustrates a cross-sectional view of the material of FIG. 7.

A cross-sectional view of the material 70 is illustrated in FIG. 8. As can be seen, the detector wires 28 are spatially separated from the emitter wires 26. The material 70 has a high dielectric constant to reduce capacitive effects, and, therefore, the emitter wires 26 and the detector wires are spatially and electrically isolated. The connector housing 20 may be formed over the material 70 through the encapsulation process after the material 70 has cured.

Figure 9:
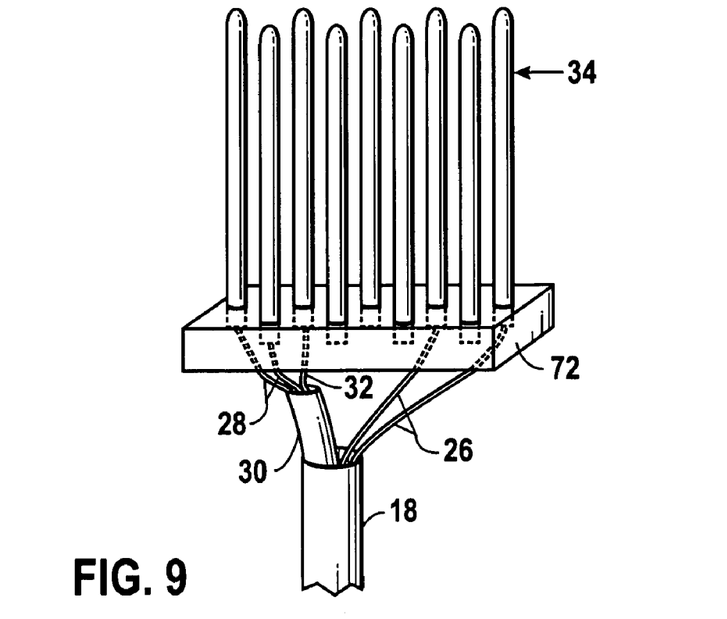
FIG. 9 illustrates a printed circuit board configured to spatially separate wires in accordance with an alternative exemplary embodiment of the present invention.

In another embodiment, a printed circuit board (PCB) 72 may also be used to maintain spatial separation between the emitter wires 26 and detector wires 28, as shown in FIG. 9. The PCB 72 may be a multi-layer PCB with solder pads or holes (not shown) for coupling the wires to the PCB 72. The solder pads or holes for coupling the emitter wires 26 to the PCB 72 may be located remotely from the solder pads or holes for coupling the detector wires 28 to the PCB 72. Vias and traces in and on the PCB 72 connect the emitter wires 26 and detector wires 28 to the proper pins. The connector housing 20 may be formed over the PCB 72.

Figure 10:
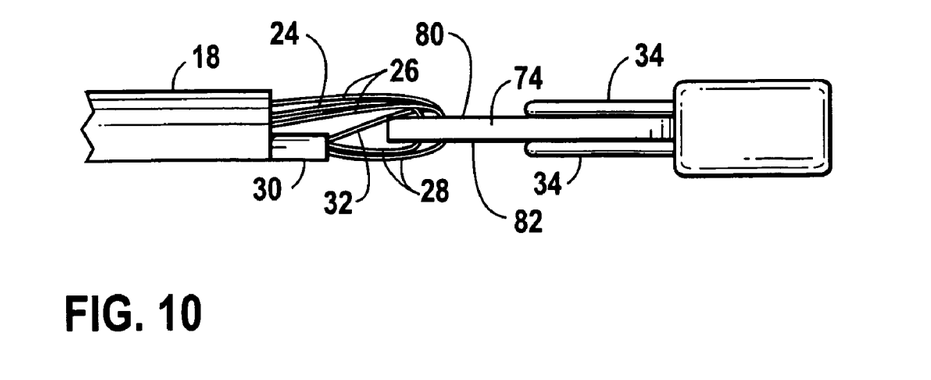
FIG. 10 illustrates an alternative embodiment for using a printed circuit board in accordance with an alternative exemplary embodiment of the present invention.
Figure 11:
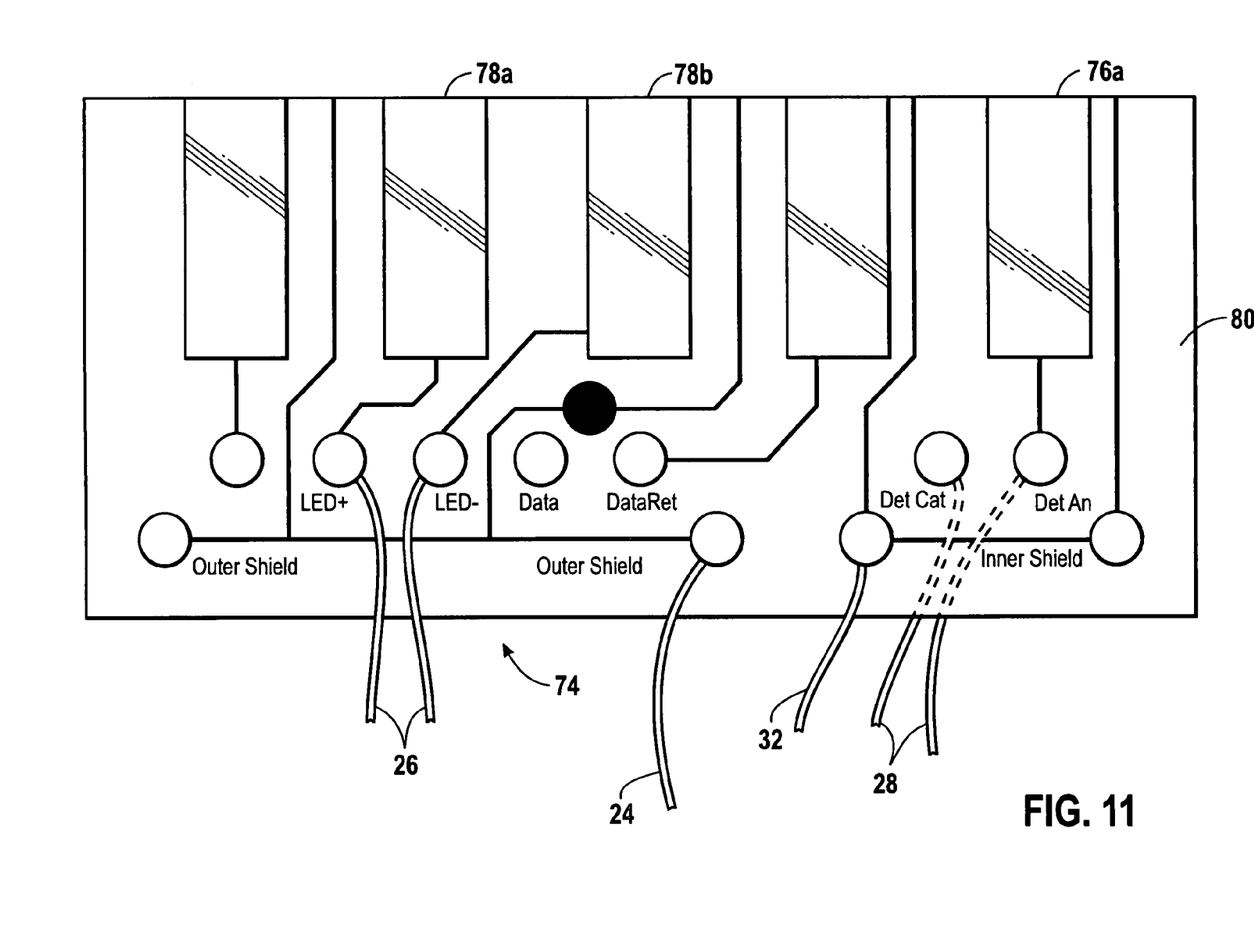
FIG. 11 illustrates top view of the printed circuit board of FIG. 10.
Figure 12:
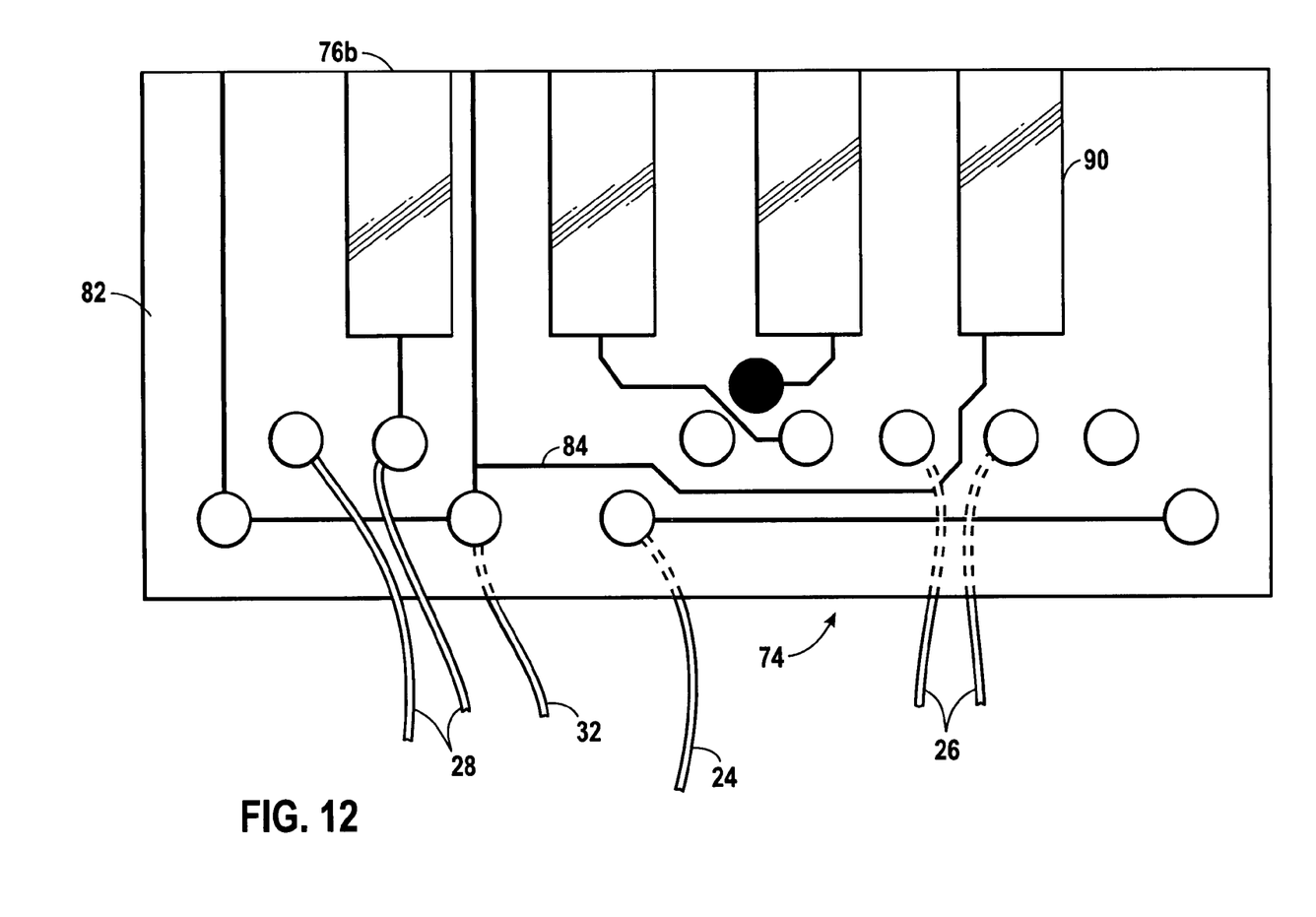
FIG. 12 illustrates a view of the bottom of the printed circuit board of FIG. 10.

An alternative embodiment using a PCB to prevent crosstalk is shown in FIG. 10. Specifically, FIG. 10 shows a side view of a PCB 74 positioned between a top layer and a bottom layer of pins 34. The PCB 74 is a two surface circuit board having traces, pads, and connection points for the connector pins 34 on both surfaces of the PCB 74. As can be seen by further referring to FIGS. 11 and 12, the detector contacts 76a-b are physically remote from the emitter contacts 78a-b. In addition, the inner shield wire 32 is soldered on the top surface 80 of the PCB 74 while the detector wires 28 are soldered on the bottom surface 82 of the PCB 74. The location of the detector wires 28 provide spatial separation from the emitter wires 26. The PCB 74 additionally shields the detector contacts 76a-b and emitter contacts 78a-b from the memory chip contacts. The inner shield 32 is routed by trace 84 to a contact pad 90 which may be conductively coupled to a pin 6 (not shown) of a connector. The connector housing 20 may be formed over the PCB 74. Wires 26 and 28 emanating from cable 18 may be kept short in length to prevent crosstalk. Use of the PCB provides an easier substrate to terminate the wires to during the manufacturing process than terminating the wires to the pins directly.

Figure 13:
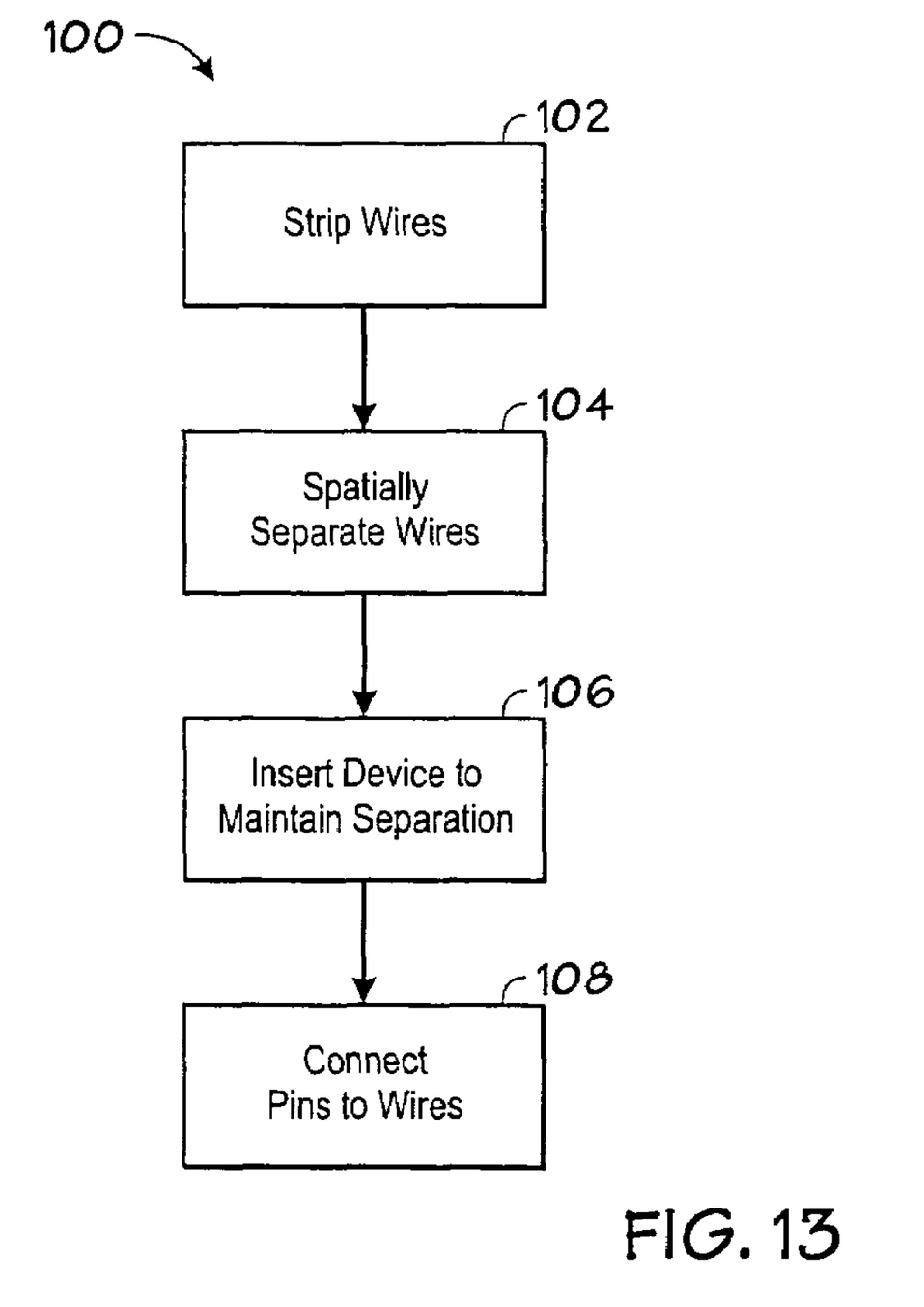
FIG. 13 is a flow chart depicting a technique for reducing crosstalk in accordance with an exemplary embodiment of the present invention.

Turning to FIG. 13, a technique to prevent crosstalk in pulse oximetry cables in accordance with an exemplary embodiment of the present invention is illustrated as a flow chart and generally designated by the reference numeral 100. The technique 100 begins by stripping a cable, as indicated at block 102. The cable may be any cable used in medical devices, such as those used in pulse oximeters and may include multiple wires which are also stripped. Once stripped, the wires are vulnerable to potential noise-inducing influences, such as crosstalk from the other wires of the cable. Therefore, the stripping of the wires should be performed with the goal of preserving as much of the shield on the wires as possible.

After the wires are stripped, the wires are spatially separated from each other, as indicated at block 104. Specifically, sets of twisted pairs are separated from each other. The spatial separation of the wires may be done by a person or by a machine. Because the twisting of the wires is a noise cancellation technique, effort should be made to keep the pairs of wires twisted, insofar as it is practicable.

The spatial separation between the sets of wires is maintained by coupling or inserting a device between the sets of wires, as indicated at block 106. Specifically, the spatial separation may be maintained by implementing one of the embodiments described above, such as using a PCB to physically separate the emitter wires 26 from the detector wires 28, for example, or inserting an insulative object between the pairs of wires. The use of one of the above mentioned exemplary embodiments, or other device, precludes the pushing of the separated wires into closer proximity of each other during the over-molding process or other processing and handling that may occur during manufacture.

Connector pins are electrically coupled to the wires, as indicated by block 108. The connector pins may be connected to the wires either directly by soldering the wires to the pins or indirectly via traces on a PCB, as described above, depending on the particular embodiment being implemented. By physically separating the wires and preserving that separation, crosstalk between wires is greatly reduced, or eliminated. The elimination of crosstalk may increase the accuracy of the medical devices.

The techniques described herein for maintaining spatial separation of the signal wires during the cable termination process to reduce cross-talk have applicability in patient monitoring applications beyond pulse oximetry. With respect to devices that utilize photo-emitters and photo-detectors as described herein, such techniques can be utilized in devices intended to monitor other blood constituents such as carboxyhemoglobin, methemoglobin, total hemoglobin content, glucose, pH, water content and others. Reducing signal crosstalk is also of importance in bio-impedance measurements for evaluating physiologic variables such as tissue hydration, cardiac output or blood pressure.

The step of creating a cabling connector may not be restricted to over-molding processes. Pre-molded connector housing components may be assembled to contain the pins and cable. During assembly, wires may come into close proximity that results in cross-talk (noise). The techniques described above may be used to reduce the likelihood of this occurring by ensuring proper spatial separation during the assembly process.

Additionally, it should be understood, that although the figures and the associated discussion describe embodiments wherein the cable 18 comprises twisted pair wires, the techniques disclosed herein may be applicable to any type of cable. Indeed, the techniques disclosed herein may be implemented with a coaxial cable, for example.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A pulse oximetry cable assembly comprising:
   a cable having a first pair of wires and a second pair of wires, wherein the first and second pairs of wires are surrounded by an outer shield and the second pair of wires are surrounded by an inner shield; and
   an insulative piece, wherein the insulative piece comprises a printed circuit board configured to maintain spatial separation between the first and second pairs of wires, the insulative piece comprising:
      a first side and a second side, wherein the first pair of wires are coupled to conductive members located on the first side of the insulative piece and the second pair of wires are coupled to conductive members located on the second side of the insulative piece, the conductive members comprising solder pads and traces coupled to the solder pads, wherein the traces and solder pads are configured to spatially separate the first pair of wires from the second pair of wires, the traces being configured to route emitter signals carried on the first pair of wires away from detector signals carried on the second pair of wires; and
      inner shield traces and outer shield traces, wherein the inner shield is coupled to the inner shield traces and the outer shield is coupled to outer shield traces, the inner shield traces being configured to encompass detector contacts on the printed circuit board and the outer shield traces being configured to encompass emitter contacts on the printed circuit board.

2. The cable assembly of claim 1, wherein the insulative piece supports a conductive piece, the conductive piece being electrically grounded and positioned in between the first and second pairs of wires.

3. The cable assembly of claim 1, comprising a sensor coupled to the first and second pairs of wires.

4. The cable assembly according to claim 1, comprising a connector for coupling the cable assembly to a pulse oximeter.

5. A device for reducing crosstalk comprising:
   a multi-surface printed circuit board comprising:
   a first surface having a first plurality of contacts, wherein a pair of emitter wires are coupled to the first surface and electrically coupled with two adjacent contacts on the first surface; and
   a second surface having a second plurality of contacts, wherein a pair of detector wires are coupled to the second surface and one wire of the pair of detector wires is electrically coupled to one of the second plurality of contacts on the second surface.

6. The device of claim 5, wherein one contact of the first plurality of contacts on the first surface is electrically coupled to another wire of the pair of detector wires.

7. The device of claim 5, wherein the first surface comprises an outer shield trace configured to surround the two adjacent contacts electrically coupled with the pair of emitter wires, wherein the outer shield trace is electrically coupled to an outer shield that surrounds the pairs of emitter and detector wires in a cable.

8. The device of claim 6, wherein the first surface comprises an inner shield trace configured to surround the one contact of the first plurality of contacts on the first surface electrically coupled to one wire of the pair of detector wires, wherein the inner shield trace is electrically coupled to an inner shield that surrounds the pair of detector wires in a cable.

9. The device of claim 8, wherein the second surface comprises an inner shield trace which is electrically coupled to the inner shield trace of the first surface, the inner shield trace of the second surface being configured to surround the one contact of the second plurality of contacts electrically coupled to one wire of the pair of detector wires.

10. The pulse oximetry cable assembly of claim 1 comprising a connector housing formed over the insulative piece.

* * * * *